(12) United States Patent
Neu (10) Patent No.: US 9,107,894 B2
(45) Date of Patent: Aug. 18, 2015

(54) FORMULATION TO IMPROVE GASTROINTESTINAL FUNCTION

(75) Inventor: Josef Neu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 644 days.

(21) Appl. No.: 12/682,815

(22) PCT Filed: Oct. 14, 2008

(86) PCT No.: PCT/US2008/079849
§ 371 (c)(1),
(2), (4) Date: Apr. 22, 2010

(87) PCT Pub. No.: WO2009/052106
PCT Pub. Date: Apr. 23, 2009

(65) Prior Publication Data
US 2010/0222271 A1    Sep. 2, 2010

Related U.S. Application Data

(60) Provisional application No. 60/979,845, filed on Oct. 14, 2007.

(51) Int. Cl.
| | | |
|---|---|---|
| *A61K 38/00* | (2006.01) | |
| *A01N 25/00* | (2006.01) | |
| *A61K 35/20* | (2006.01) | |
| *A23L 1/30* | (2006.01) | |
| *A23L 2/00* | (2006.01) | |
| *A23J 1/00* | (2006.01) | |
| *A61K 31/22* | (2006.01) | |
| *A61K 31/198* | (2006.01) | |
| *A61K 31/202* | (2006.01) | |
| *A61K 31/65* | (2006.01) | |
| *A61K 38/01* | (2006.01) | |

(52) U.S. Cl.
CPC ............ *A61K 31/22* (2013.01); *A61K 31/198* (2013.01); *A61K 31/202* (2013.01); *A61K 31/65* (2013.01); *A61K 38/011* (2013.01)

(58) Field of Classification Search
None
See application file for complete search history.

(56) References Cited

U.S. PATENT DOCUMENTS

| | | | |
|---|---|---|---|
| 5,229,136 A | * | 7/1993 | Mark et al. ............. 424/535 |
| 2004/0097404 A1 | | 5/2004 | Kessler et al. |
| 2006/0229256 A1 | * | 10/2006 | Anthony et al. ........... 514/19 |

FOREIGN PATENT DOCUMENTS

WO    WO 99/49741    10/1999

OTHER PUBLICATIONS

Dietary Reference Intakes 2006. National Academy of Sciences.: pp. 529-541.*
Health Supplements Nutritional Guide, Based on Dietary Reference Intakes Food and Nutrition Board of the Institute of Medicine, National Academy of Sciences, 1997-2001.*
Chesney et al. 1998, Taurine 3, pp. 463-476.*
Sharpless et al. 1997. J. of AOAC International 80:611-621.*
Campoy et al. 1998. Early Human Dev. 53:Supl 149-64.*
Evans et al., "Intestinal fuels: glutamine, short-chain fatty acids, and dietary fiber," *Journal of the American Dietetic Association*, Oct. 1992, pp. 1239-1246, 1249, vol. 92, No. 10.
Van Den Berg et al., "Glutamine-enriched enteral nutrition in very low birth weight infants. Design of a double-blind randomised controlled trial [ISRCTN3254583]," *BMC Pediatrics*, Sep. 2004, pp. 17, vol. 4, No. 1.
Kolar, S.S.N., et al., "Docosahexaenoic Acid and Butyrate Synergistically Induce Colonocyte Apoptosis by Enhancing Mitochondria $Ca^{2+}$ Accumulation," *Cancer Research*, Jun. 1, 2007, pp, 5561-5567, vol. 67, No. 11.
Takano, Y., et al., "Modulation of the Intestinal $Ca^{2+}$ Uptake by a Cheese Whey Protein Digest," *Biosci. Biotechnol. Biochem.*, Jun. 7, 2007, pp. 1487-1493, vol. 71, No. 6.

* cited by examiner

*Primary Examiner* — Shulamith H Shafer
(74) *Attorney, Agent, or Firm* — Saliwanchik, Lloyd & Eisenschenk (57) ABSTRACT

The subject invention provides compositions, and uses thereof, that improve gastrointestinal function. The compositions and methods of the subject invention are particularly advantageous for use with neonates because they can be used to stimulate development of the immature intestine in order to provide an enhanced ability to absorb nutrients and attain a stronger barrier function.

19 Claims, 3 Drawing Sheets

FORMULATION TO IMPROVE GASTROINTESTINAL FUNCTION

CROSS REFERENCE TO RELATED APPLICATION

This application is a national stage application of International Application Number PCT/US2008/079849, filed Oct. 14, 2008; which claims the benefit of U.S. Provisional Application Ser. No. 60/979,845, filed Oct. 14, 2007, which are hereby incorporated by reference herein in their entirety, including any figures, tables, or drawings.

BACKGROUND OF THE INVENTION

The intestine serves a barrier function that is a critical component of the innate immune system. Only a single layer of epithelial cells separates the luminal contents from effector immune cells in the lamina propria and the internal milieu of the body. Breaching this single layer of epithelium can lead to pathologic exposure of the highly immunoreactive subepithelium to the vast number of microbes and antigens in the lumen. Breakdown of the barrier is implicated in the pathogenesis of acute illnesses such as multiple organ system failure and bacterial translocation leading to sepsis.

Defective functioning of the intestine as a barrier against infection can occur in individuals of all ages. However, the elderly and the very young are particularly suspectible. For example, because of feeding intolerance and the fear of necrotizing enterocolitis (NEC), many premature infants undergo a period of "luminal starvation" during which time these infants receive very little, if any, food via the gastrointestinal tract and are nourished primarily by the intravenous route with total parenteral nutrition (TPN). A lack of enteral nutrients with TPN contributes to mucosal breakdown, bacterial translocation and an increased propensity to systemic inflammation (Huang Y, Li N, Liboni K, Neu J "Glutamine decreases endotoxin-induced IL-8 production in Caco-2 cells via non-NF kappa-B pathways" *Cytokine.* 2003 May; 22(3-4): 77-88).

The preterm, especially the very low birthweight preterm infant, is frequently also highly stressed because of respiratory insufficiency, thermoregulation, and other challenges. The trend in the past decade has been to provide greater amino acids by the parenteral route (Liboni K, Li N, Neu J. "Mechanism of Glutamine-mediated amelioration of lipopolysaccharide-induced IL-8 production in Caco-2 cells" *Cytokine.* 2004 Apr. 21; 26(2):57-65; Beierle E A, Chen M K, Hartwich J E, Iyengar M, Dai W, Li N, Demarco V, Neu J. "Artificial rearing of mouse pups: development of a mouse pup in a cup model" *Pediatr Res.* 2004 August; 56(2): 250-5.) in the acute phase of illness in the first weeks after birth, then to transition to human milk or formula by the enteral route. This is inadequate because any enteral nutrition provided in the first weeks of life is usually in the form of "minimal enteral nutrition" (roughly defined as an amount of nutrition that does not meet the nutritional requirements for growth but confers some benefit, and is usually less than 20% of the total nutritional requirements) (Liboni, K, Li N, Scumpia P O, Neu J. "Glutamine Modulates LPS-Induced IL-8 Production. Through IκB/NF-κB in Human Fetal and Adult Intestinal Epithelium" *Journal of Nutrition* 2005 February; 135(2): 245-51; Liu Z, Li N, Neu J. "Tight junctions, leaky intestines and pediatric diseases" *Acta Paediatrica* 2005; 94:386-393; Zhang L, Li N, Caicedo R, Neu J. "Lactobacillus Rhamnosus G G Dead or Alive Decreases Tumor Necrosis Factor-α Induced IL-8 Production in Caco-2 cells" *Journal of Nutrition* 2005 July; 135(7):1752-6.)

Despite often being termed "trophic nutrition" minimal enteral nutrition along with parenteral nutrition (PN) does not provide a significant trophic effect on the intestine nor does it enhance barrier function (Zhang L, Li N, desRobert C, Fang M, Liboni K, McMahon R, Caicedo R, Neu J. "Lactobacillus Rhamnosus GG Decreases Lipopolysaccharide-Induced Systemic Inflammation in A Gastrostomy-Fed Infant Rat Model" Journal of Pediatric Gastroenterology and Nutrition May, 2006 42:545-552; Neu, J. "The 'myth' of asphyxia and hypoxia-ischemia as primary causes of necrotizing enterocolitis" Biol Neonate. 2005; 87(2):97-8; Neu J, Chen M, Beierle E "Intestinal innate immunity: how does it relate to the pathogenesis of necrotizing enterocolitis?" *Semin Pediatr Surg.* 2005 August; 14(3):137-44). Moreover, it is clear that the use of TPN is significantly associated with hospital acquired sepsis (Caicedo R A, Schanler R J, Li N, Neu J. "The developing intestinal ecosystem: implications for the neonate" *Pediatr Res.* 2005 October; 58(4):625-8), which is partially caused by translocation of intestinal bacteria (Li N, Lassman B J, Liu Z., Liboni, K., Neu, J. "The Effects of Protein Deprivation on Growth and Small Intestine Morphology Are Not Ameliorated By Glutamine or Glutamate in Gastrostomy-Fed Rat Pups" J. Pediatric Gastroenterology and Nutrition 2004 July; 39(1):28-33; Neu J, Zhang L. "Feeding intolerance in very-low-birthweight infants: what is it and what can we do about it?" *Acta Paediatr Suppl.* 2005 October; 94(449):93-9).

Although the recent trends toward early increases in intravenous protein intake may provide benefits in terms of protein synthesis, decreased catabolism, and perhaps even somatic growth (Beierle E A, Chen M K, Hartwich J E, Iyengar M, Dai W, Li N, Demarco V, Neu J. "Artificial rearing of mouse pups: development of a mouse pup in a cup model" *Pediatr Res.* 2004 August; 56(2): 250-5; Neu J. "Gastrointestinal maturation and feeding" *Semen Perinatal.* 2006 April; 30(2):77-80), this practice does not promote or maintain gastrointestinal barrier function or optimal growth of the GI tract, which is a prerequisite for modulation of several disease processes where intestine mediated breakdown and systemic inflammation play a role. These include NEC, hepatic inflammation, chronic lung disease and progression of periventricular leukomalacia.

There is thus a great need for enteral adjuncts shortly after birth that will decrease the need for parenteral nutrition. A safe and effective "starter formula" that enhances intestinal growth and improves barrier function is needed for sick low birthweight infants. Such a preparation would be used as an adjunct to early aggressive parenteral nutrition and other enteral nutrients such as human milk.

BRIEF SUMMARY

The subject invention provides compositions, and uses thereof, that improve gastrointestinal function. The compositions and methods of the subject invention are particularly advantageous for use with neonates because they can be used to stimulate development of the immature intestine in order to provide an enhanced ability to absorb nutrients and attain a stronger barrier function.

In a specific embodiment, the subject invention provides a hypo-osmolar, protein enriched, minimal enteral nutrition formula with added glutamine (GLN), docosahexaenoic acid (DHA), and butyrate. The compositions of the subject invention are specifically designed to stimulate better intestinal growth, enhance the intestinal barrier and control intestine derived inflammation.

In accordance with the subject invention, protein acts by promoting intestinal protein accretion and prevention of catabolism; GLN promotes interepithelial junction integrity, minimizes the mucosal stress response and decreases inflammation; butyrate increases proliferation, enhances barrier function and increases intestinal secretion of glucagon-like peptide 2 (GLP-2, a highly intestinotrophic peptide) and DHA acts by decreasing the inflammatory response.

The formulation of the subject invention containing high levels of protein, DHA, glutamine and butyrate, but with relatively low carbohydrate and fat concentrations can be used to safely prevent intestinal barrier breakdown, prevent intestinal atrophy, and damage to distal organs such as liver and brain, when the patient is subjected to inflammatory stress.

DETAILED DISCLOSURE

The subject invention provides safe and effective compositions and methods that enhance intestinal growth and improve barrier function for low birth weight infants as well as others.

Premature or critically ill infants are often administered prolonged parenteral nutrition (total parenteral nutrition; TPN) via intravenous route due to vulnerabilities of their immature gastrointestinal tract. Unfortunately, prolonged parenteral nutrition is associated with intestinal atrophy, increased bacterial translocation, sepsis, and systemic inflammation, which can exacerbate liver, lung, and central nervous system damage leading to lifelong disability.

Current methods for addressing this problem consist of providing amino acids by the parenteral route in the acute phase of illness in the first weeks after birth, then transitioning to human milk or formula by the enteral route. This approach is inadequate because any enteral nutrition provided in the first weeks of life is usually in the form of minimal enteral nutrition, which does not provide a significant trophic effect on the intestine nor do they enhance barrier function. Moreover, the use of TPN is significantly associated with hospital acquired sepsis.

Preferably, apart from Arg and/or Gln or Glu, the composition of the subject invention has less than 20% by weight of free amino acids, more preferably the composition has less than 20% free amino acids, even more preferably, the composition has less than 15% free amino acids, and the composition may also have less than 10%, 5%, or 1% free amino acids.

Intestinal mucosal integrity relates to several functional capabilities including digestion, absorption, bacterial or antigenic translocation, and the capability for luminal microorganisms and/or toxins to incite an inflammatory response causing pathology such as necrotizing enterocolitis or systemic inflammation.

In one embodiment, the subject invention provides a "starter" enteral nutrition formula for very low birth weight infants that can be utilized shortly after birth. Advantageously, this formula supports intestinal development and reduces the need for parenteral nutrition, which accounts for major morbidity as well as high costs of neonatal intensive care.

In one embodiment, the compositions of the subject invention can be used as an adjunct to early aggressive parenteral nutrition and other enteral nutrients such as human milk.

The subject invention addresses one of the most important problems facing babies who are critically ill and/or born prematurely. Vulnerabilities of their immature gastrointestinal tract necessitate prolonged parenteral nutrition, which is associated with intestinal atrophy, increased bacterial translocation, sepsis, and systemic inflammation. These conditions can, in turn, exacerbate liver, lung and central nervous system damage leading to lifelong disability. Advantageously, the subject invention can be utilized via the gastrointestinal tract. In a preferred embodiment, the formulation of the subject invention utilizes adjunctive nutritional agents that enhance intestinal growth, barrier function and regulate intestine-derived inflammation and stress responses.

The methods and compositions described herein are particularly useful for neonates weighing less than 1250 grams. These neonates have very immature gastrointestinal tracts. Neonatologists are reluctant to nourish these babies using their gastrointestinal tracts and, instead, nourish them primarily through the intravenous route, which is associated with significant problems such as hospital acquired sepsis. The earlier the gastrointestinal tract in these babies can be used, the less the risk for hospital acquired sepsis, which affects about 30-40% of these babies during their hospitalization and causes significant morbidity and markedly increases the cost of hospitalization.

The materials and methods of the subject invention has other uses including, for example, such as helping patients at all ages recover from bowel surgery.

Specifically exemplified herein is a hypo-osmolar, protein enriched, minimal enteral nutrition formula with added glutamine (GLN), docosahexaenoic acid (DHA), and butyrate that is specifically designed to stimulate better intestinal growth, enhance the intestinal barrier and control intestine-derived inflammation. The hypo-osmolar formulation containing high levels of protein, DHA, GLN and butyrate, but with relatively low carbohydrate and fat content can be used to prevent intestinal barrier breakdown and prevent intestinal atrophy in comparison to a minimal enteral nutrition formulation containing the usual mixture of macronutrients.

Preferably, the protein content of the composition is more than 2% by weight, more than 3% by weight, more than 5% by weight, more than 7.5% by weight, and/or more than 10% by weight.

Preferably, the carbohydrate content is less than 10% by weight, less than 7.5% by weight, and/or less than 5% by weight.

Preferably, the fat content is less than 10% by weight, less than 7.5% by weight, and/or less than 5% by weight.

The combination of GLN, DHA, and butyrate in a high protein, low fat and carbohydrate, hypo-osmolar formula acts synergistically to increase mucosal mass and decrease intestinal hyperpetineability and damage due to intestine derived inflammation. These benefits are achieved through a combination of stabilizing mucosal barrier and decreasing intestine derived inflammation.

The combination formula of the subject invention is safe and offers greater effects than seen with any of the individual nutrient supplements.

The formulations of the subject invention can be used to provide the following advantages:
1. High protein to promote intestinal trophism and barrier function.
2. Glutamine to prevent intestine derived inflammation, and modulate stress-related apoptosis.
3. Omega 3 fatty acids, such as DHA, to prevent propagation of intestine derived inflammation.
4. A short chain fatty acid, such as butyrate, to promote barrier function.

Protein intake via the gastrointestinal (GI) tract is the main determinant of intestinal mucosal growth. In certain individuals, including premature and/or low birthweight infants, dietary protein needs to be supplied in sufficient quantities by the enteral route to prevent mucosal breakdown and promote barrier function. Furthermore, glutamine (GLN), butyrate and DHA are beneficial as supplements to enhance intestinal barrier function and prevent the propagation of intestine-derived inflammatory response and to prevent stress-related distal organ apoptosis.

The protein component of the subject invention may be, for example, whey or casein. In a preferred embodiment, the primary protein component is whey. Preferably, the protein is provided as about 0.5 to 1 gram/Kg/day.

The glutamine component of the formulation of the subject invention may be provided as an individual amino acid or as part of, for example, a dipeptide. In a preferred embodiment, glutamine is provided in the formula as an individual amino acid. In one embodiment, arginine is also included in the formulation. One embodiment comprises the use of an arginyl-glutamine dipeptide. Arginine and glutamine may also be provided individually in the formula. The dose of glutamine can be, for example, 0.3 to 0.7 gram/Kg/day.

In one embodiment, the subject invention comprises administering an omega 3 fatty acid, especially a long chain polyunsaturated fatty acid (PUFA), such as DHA, in order to provide a beneficial role to the infant small intestine by down-regulation of proinflammatory mediators. The dose of DHA can be, for example, 0.1 to 1 gram/Kg/day. Arachidonic acid (AA) and/or eicosapentanoic acid (EA) can also be administered in accordance with the subject invention. The ratio of DHA to AA or EA would typically be in the range of 5:1 to 1:1.

Short chain fatty acids (SCFA) can play a role in maintaining the mucosal barrier in the gut. These SCFAs are a product of bacterial metabolism of carbohydrates, and may be partially responsible for the beneficial effects of commensal bacteria or probiotics. The SCFAs can therefore be considered as "postbiotics". There is currently concern pertaining to the use of probiotics for premature infants, partially based on safety concerns in providing live bacteria to immunocompromised hosts. Butyrate can be used according to the present invention to provide the benefits of probiotic bacteria without deleterious side effects. The dose of butyrate can be, for example, 100-800 mg/Kg/day.

In accordance with the subject invention, higher intakes of butyrate can be used to increase tight junction protein (claudin and occluding) expression along with decreasing ev-vivo permeability to paracellular markers. The use of butyrate also down-regulates the inflammatory response in the small intestine and prevents its propagation to distal organs along with some of the pathology that can be seen in the liver, lung and brain due to inflammation.

The formulations of the subject invention can be used as a adjunct to early aggressive parenteral nutrition and other enteral nutrients such as human milk, that improve neonatal health and decrease the morbidity and costs associated with a lack of enteral nutrition and long term parenteral nutrition.

In a further embodiment, the formulation of the subject invention can be used to improve wound healing in intestinal surgery and to ameliorate symptoms of inflammatory bowel diseases.

As described in detail below, the efficacy of the formulation of the subject invention has been evaluated with the infant rat pup in the cup gastrostomy feeding model to evaluate in a step-wise fashion the effects of supplementing a "starter formula" with: 1) high protein; 2) GLN; 3) DHA; and 4) butyrate. The formulation has been evaluated with regard to intestinal barrier function, intestine derived inflammation, propagation of inflammation and distal organ pathology under non-inflammatory and inflammatory conditions.

Rat studies with respect to the current invention demonstrated the following:
1. Protein deprivation (25% normal intake) is associated with intestinal villus atrophy.
2. Neither GLN nor GLU can rescue this effect, but higher protein intake is associated with increased intestinal claudin levels.
3. A normal protein formula (which is equal to the intake derived when the rat pups are nursing from the mothers) does not prevent LPS initiated CINC or TNF$\alpha$ production by the intestine.
4. However, GLN supplementation in protein deprived, LPS-treated rats decreases CINC (rodent form of IL-8—a potent neutrophil chemoattractant) production by the intestine.
5. Decreased intestinal CINC production with GLN supplementation is associated with decreased intestinal myeloperoxidase and morphologic markers of inflammation.
6. The GLN-induced decreased intestinal CINC is associated with lower plasma CINC and TNF-$\alpha$ levels suggesting that this effect could translate to decreased inflammation and injury to extraintestinal organs.
7. Administration of NaB to BBDP rats, a strain known to have a highly permeable intestine prior to the development of diabetes, can decrease mortality due to diabetes via downregulation of the inflammatory response, putatively secondary to maintenance of improved intestinal mucosal integrity.

Cell culture studies support that GLN deprivation:
1. Decreases transcpithelial resistance, increases permeability and decreases claudin protein expression.
2. Exacerbates LPS and TNF$\alpha$ induced IL-8 production in cells derived from human adults and fetuses. Cells derived from the human fetus (H4) are exquisitely more sensitive to LPS and GLN deprivation than adult (Caco-2) derived cells.
3. In adult derived cells acts through increased proteolysis of I$\kappa$B, allowing greater release, nuclear translocation and DNA binding of NF$\kappa$B, but in fetal derived cells acts through decreased translational activation (decreases eIF-$\alpha$), thus decreasing I$\kappa$B, allowing greater release, nuclear translocation and DNA binding of NF$\kappa$B.

Cell culture studies of n-6 and n-3 LCPUFAs and butyrate:
1. Show that DHA can down regulate TNF$\alpha$-induced inflammation.
2. Show that DHA can down regulate the inflammatory response induced by the Toll like receptor ligand poly I:C.
3. Show that butyrate markedly increases transepithelial resistance, a major marker of paracellular integrity, in Caco-2 cells.

Studies of GLN deprivation in intestinal epithelial cells show decreased claudin-1, occludin, and ZO-1 protein expression by Western blot and disappearance of perijunctional claudin-1 and a reduction of occludin by immunofluorescence microscopy. Transmission electron microscopy revealed that GLN deprived cells formed irregular junctional complexes between the apical lateral margins of adjoining cells.

Following are examples which illustrate procedures for practicing the invention. These examples should not be construed as limiting. All percentages are by weight and all solvent mixture proportions are by volume unless otherwise noted.

Example 1

The nutritional value of GLN may be influenced by the highly polarized nature of the mucosal epithelium such that GLN provides a nutritional advantage when the same concentrations are provided apically or basally. Apical versus basal GLN uptake kinetics were compared and found not to differ significantly or result in significant differences in differentiation. It was found that the absence of GLN (no GLN added to the media and GLN synthetase inhibition) caused a significant decrease in transepithelial resistance (TER) and increase in permeability.

A similar effect was seen in vivo. In Caco-2 cell culture, the effect of GLN deprivation was most marked when GLN synthetase (GS) was also inhibited, but could also be elicited without GS inhibition when the cell cultures were stressed with media change.

Differentiation of Caco-2 cells as evaluated with alkaline phosphates activity was also markedly dependent on GLN. When GLN synthetase activity was inhibited with MS, glutamate could not "rescue" the recovery of alkaline phosphatase; whereas GLN administered to the cell culture medium fully recovered the alkaline phosphatase activity.

Studies were conducted to evaluate whether glutamate, a mixture of nucleotide monophosphates, arginine, or glucosamine could support proliferation of rat intestinal crypt cells (IEC-6) in the absence of GLN. The results showed that in the absence of exogenous GLN, glutamate, glucosamine, arginine or nucleotide monophosphates yielded similar proliferation as GLN. GLN synthetase inhibited cells treated with glutamate, glucosamine, arginine, or nucleotide mixture showed a decrease in proliferation compared with cells treated with GLN across all treatment doses. This suggests the necessity of an active GLN synthetase for the conversion of these precursors to GLN or a compound that exhibits the same effects on cell proliferation as GLN.

Example 2

The Effects of GLN and Glutamate on Caco-2 Cell Intercellular Junction Morphology and Tight Junction Proteins Using the "pup-in-a-cup" rat model, protein deprivation and supplementation with GLN or GLU in the developing rat small intestine were examined. Four groups of 6-7 d old pups were fed via a gastrostomy tube providing 100% or 25% protein (relative to mother fed rats) rat milk substitute (RMS) with and without additional GLN or glutamate (GLU) for 6 d. Pups receiving the 100% protein RMS experienced better growth than the 3 groups of pups receiving the 25% protein RMS+/−GLN/GLU supplementation. Thus, better growth can be achieved with enteral protein supplementation, and neither GLN nor GLU alone can rescue the effects of protein deprivation.

Villus size is a major component of absorptive capability. Villus height and area were greater in pups receiving the 100% protein RMS compared to 3 groups given the other RMS formulas, whereas villas height and area did not differ between the groups receiving 25% protein with or without GLN or GLU. Thus, protein intake is critical for maintenance of villus size.

Example 3

Effect of High Protein Diet on Tight Junction Proteins

The tight junction proteins play an integral role in paracellular permeability of the intestinal barrier, and two of these, claudin and occludin were evaluated using Western blotting. Tight junction protein claudin-1 was significantly higher in the group fed the 100% protein diet, while occludin did not differ among the 4 groups.

Example 4

CINC mRNA

Cytokine induced neutrophil chemoattractant (CINC) is a rodent chemokine that performs neutrophil chemoattractant functions similar to IL-8 in the human. Large quantities of this proinflammatory mediator can be detrimental. Intestinal CINC is significantly increased with enterally administered LPS.

To clarify the effects of diets on the CINC mRNA in small intestine, RT-PCR was performed. Protein deprivation and LPS (25% protein-only group) increased CINC mRNA expression. GLN supplementation decreased CINC mRNA to a level similar to mother-fed animals. Densitometry shows that the 25% protein-fed rat intestine had a significantly higher level of CINC mRNA compared with mother-fed pups, and GLN reversed this effect. However, Glu did not show the same effect as GLN.

Example 5

CINC Peptide

Intestinal CINC peptide in the LPS treated pups provided 100% and 25% protein was elevated about 13 fold compared to the mother reared pups. GLN and GlU decreased intestinal CINC peptide by 73 and 80%, respectively. Gastrostomy fed, LPS treated pups also had a higher level of plasma CINC peptide. GLN, but not Glu decreased plasma CINC peptide.

Example 6

Myeloperoxidase Reflects the Neutrophil Infiltration and Activity at the Site of Inflammation An approximate 6-fold elevation of intestinal myeloperoxidase (MPO) activity in the gastrostomy fed, LPS treated rats was decreased by GLN and Glu by 92% and 54%, respectively.

The studies in the rat pup demonstrated that protein depletion causes significant intestinal atrophy that cannot be rescued with GLN or GLU. However, in a second set of studies (inflammatory conditions), protein does not decrease the LPS induced CINC production by the intestine, but GLN does. This suggests that the combination of nutrients (enteral protein and added GLN) might be synergistic in preventing intestinal atrophy (protein effect) and decreasing inflammation (GLN effect). These studies also support that manipulation of enteral GLN can alter intestinal junction integrity and that this may relate to initiation and propagation of intestinal inflammation.

Example 7

Effect of Butyrate on Intestinal Interepithelial Junctions

Figure 1:
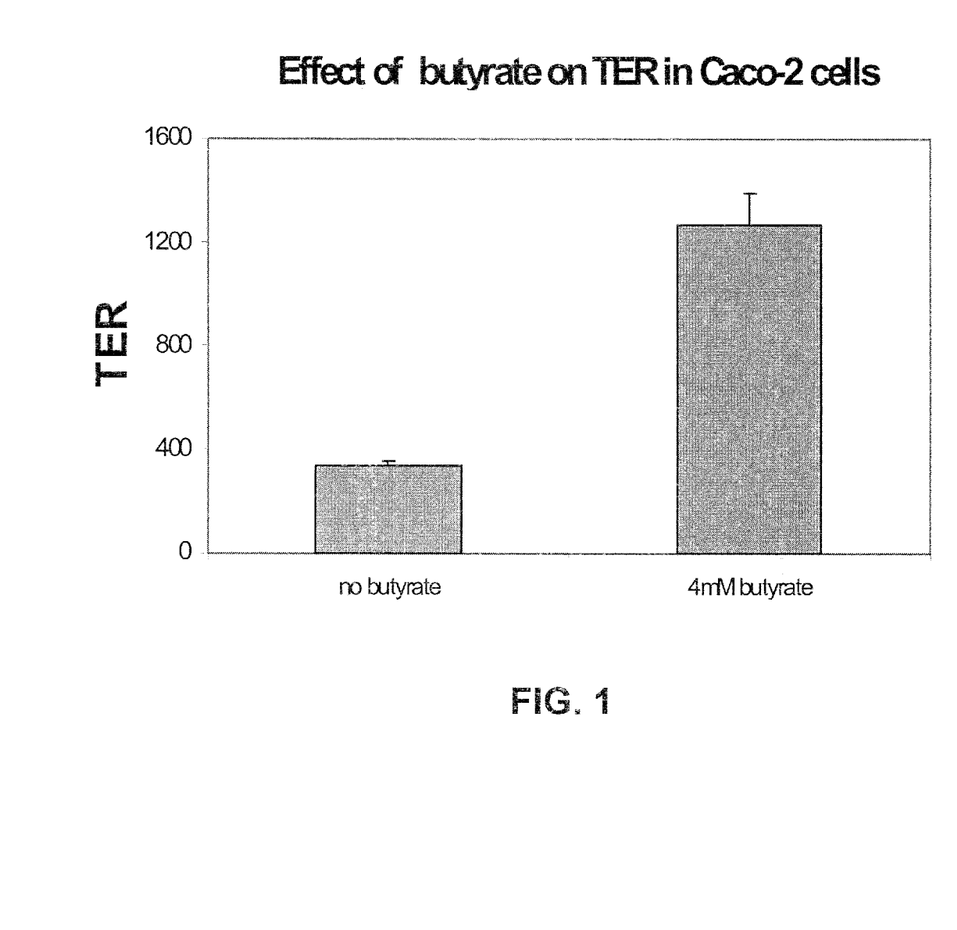
FIG. 1 shows the increase mediated by butyrate on early confluent Caco-2 cells transepithelial resistance after 24 hours of treatment.

Studies in Caco-2 cells show that butyrate has a marked effect on intestinal interepithelial junctions. FIG. 1 shows the profound increase mediated by butyrate on early confluent Caco-2 cells transepithelial resistance after 24 hours of treatment.

Example 8

Omega 3 Fatty Acids

The effects of omega 3 fatty acids were evaluated in intestinal epithelial cell cultures as a preliminary model prior to their evaluation in vivo in the pup in the cup model. The data show significant anti-inflammatory effects in the intestinal epithelial cells.

The anti-inflammatory properties of two major dietary n-3 long-chain polyunsaturated fatty acids (PUFA), eicosapentaenoic acid (EPA, 20:5 n-3) and docosahexaenoic acid (DHA, 22:6 n-3) have been used clinically to treat the symptoms of inflammatory diseases (Calder, P. C. "Polyunsaturated fatty acids and inflammation". *Biochem. Soc. Trans.*, 2005. 33:423-427).

EPA and DHA were used as n-3 PUFA and linoleic acid (LA, 18:2 n-6) as n-6 PUFA. The H4 and Caco-2 cells were pretreated with different doses of EPA, DHA and LA separately and in different combinations for 24 hours. Then TNF-α (1 µg/L for H4, 50 µg/L for Caco-2 cells) was added to cell culture medium and the cells were incubated for another 24 hours. The lower dose used in the H4 cell line reflects their exquisite sensitivity to inflammatory stimuli.

Figure 2A:
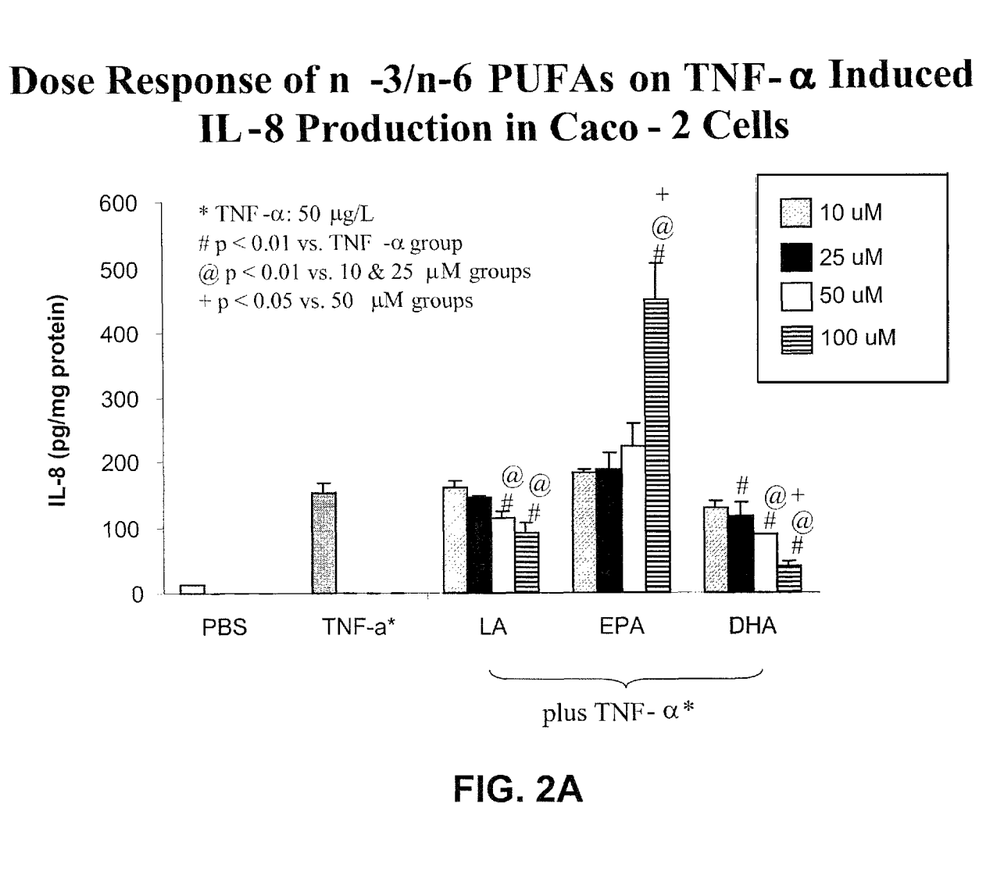
FIG. 2A-B shows the effects of different doses of the fatty acids on TNFα-induced IL-8 production.
Figure 2B:
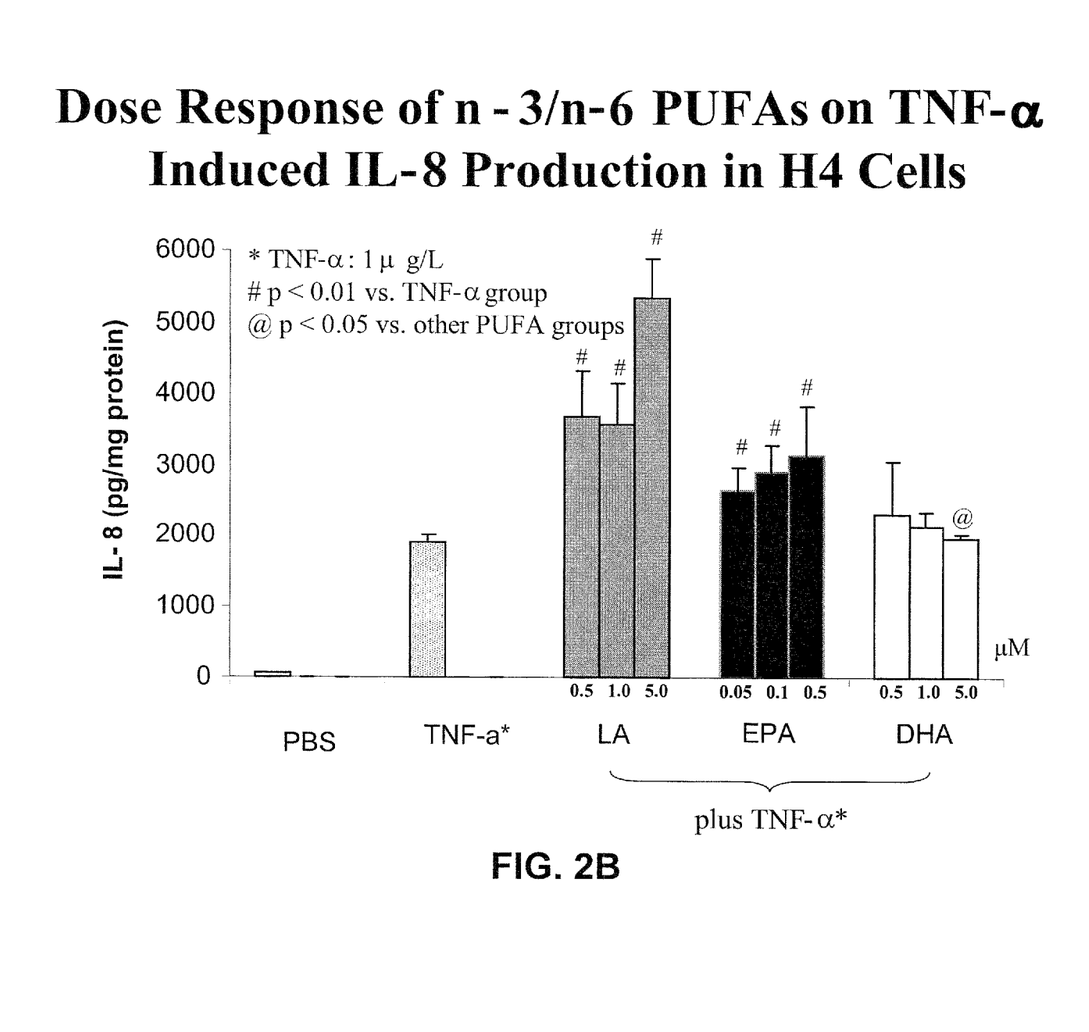

The effects of different doses of fatty acids on TNFα-induced IL-8 production were evaluated and are seen in FIGS. 2A-B.
Summary of LCPUFA Studies:
1. H4 (fetal) cells are much more sensitive to TNF-α and PUFA stimulation than Caco-2 (adult) cells.
2. Both LA and EPA showed greater inflammatory effects on IL-8 production in H4 than in Caco-2 cells with and without TNF-α stimulation.
3. DHA showed anti-inflammatory effect on Caco-2 and did not aggravate the TNF-α induced IL-8 production in H4 cells. These studies suggest the value of adjunctive DHA supplementation rather than LA or EPA.

Example 9

Effect of PUFA on Poly IC induced IL-8 Production in Intestinal Epithelium

In order to determine whether DHA has an effect on inducers of inflammation other than TNFα, stimulation of another Toll-like receptor was evaluated. Polyriboinosinic polyribocytidylic acid [poly(I:C)] is a synthetic double-stranded RNA that is used experimentally to model viral infections. It has recently been identified as one of the critical stimuli for toll like receptor 3 (TLR3). The effects of n-3 PUFA on viral induced inflammation in intestinal epithelia have not been reported.

Docosahexaenoic acid (DHA, 22:6 n-3) was used as n-3 PUFA and linoleic acid (LA, 18:2 n-6) as n-6 PUFA. Differentiated Caco-2 cells were pretreated with various doses of DHA or LA for 24 hours. The cells were then treated with poly (I: C) 50 ug/ml for another 24 hours. The culture medium was collected to measure the IL-8 production by ELISA. The first experiment determined the effect of Poly (I: C) on stimulation of IL-8, a major pro-inflammatory chemokine. Poly (I:C) increased IL-8 production by 10 fold.

The effects of DHA and LA on poly (I:C) induced IL-8 production were evaluated. DHA (100 µM) decreased poly (I:C)-induced IL-8 production by 75%. However, LA at doses of 50 and 100 µM did not significantly reduce IL-8 production induced by Poly IC.

These results show that polyunsaturated fatty acids, especially DHA, a n-3 PUFA, inhibit poly (I: C) induced IL-8 production in Caco-2 intestinal cells, suggesting that DHA may play an important role in the anti-inflammatory response caused by viral infection in intestinal epithelia.

Example 10

Nutritional Composition for Enteral Administration

The inventive composition is preferably a nutritional composition for enteral administration. That is, it is designed for oral, intragastric, or transpyloric use. The composition of the invention may be an infant formula or adult nutritional composition that can be milk-based, soy-based, or based on other food sources. The composition may be prepared as a powder or liquid nutritional composition for formulas prepared for infant, pediatric and adult populations. The inventive composition may be prepared as a nutritionally complete diet by including vitamins and minerals at acceptable levels. The subject composition can be in the form of a dietary product such as an infant formula, milk substitute, and meal replacement or supplement.

In one embodiment, a novel infant formula is nutritionally complete. By the term "nutritionally complete" is meant that the composition contains adequate nutrients to sustain healthy human life for extended periods. The infant formula of the invention contains ingredients which are designed to meet the nutritional needs of the human infant namely, protein and other nutrients such as vitamins and minerals.

The composition of the invention can contain a nitrogen source (i.e., amino acids and/or protein) in an amount that is typically about 1 g to about 10 g per 100 kcal of total composition, preferably about 2 g to about 6 g per 100 kcal. The amount of vitamins and minerals in the nutritionally complete composition is typically sufficient to meet 100% of the U.S. recommended daily intake (RDI) in about 500 to about 3,000 kcal, preferable is about 1,000 to about 3,000 kcal.

In one embodiment of the present nutritional composition the amount of vitamins and minerals is sufficient to meet 100% of the RDI in about 500 to about 3,000 kcal, preferably in about 1,000 to about 3,000 kcal. As used herein, the RDI's are intended to mean those published in the Federal Register, Vol. 58, No. 3, Wednesday, Jan. 6, 1993, page 2227 which are as follows: Vitamin A, 5,000 International Units; Vitamin C, 60 milligrams; Thiamin, 1.5 milligrams; Riboflavin, 1.7 milligrams; Niacin, 20 milligrams; Calcium, 1.0 gram; Iron, 18 milligrams; Vitamin D, 400 International Units; Vitamin E, 30 International Units; Vitamin $B_6$, 2.0 milligrams; Folic acid, 0.4 milligrams; Vitamin $B_{12}$, 6 micrograms; Phosphorus, 1.0 gram; Iodine, 150 micrograms; Magnesium, 400 milligrams; Zinc, 15 milligrams; Copper, 2 milligrams; Biotin, 0.3 milligram; Pantothenic acid, 10 milligrams.

In one embodiment, the novel infant formula contains the glutamine, in an amount that is less than 0.1% by weight of the formula. It is preferred that the amount of glutamine in the formula is from about 0.001% to 0.098% by weight of the formula, more preferred is an amount of from about 0.01% to 0.098% by weight.

In the present method, the subject infant formula or dietary supplement is administered to an infant in an amount that is sufficient to promote gastrointestinal health. In a preferred embodiment, that amount is from about 0.001 to about 10,000 mg/kg of body weight of the subject per day, more preferred is an amount of from about 0.01 to about 1000 mg/kg/day, yet more preferred is about 0.01 to about 50 mg/kg/day, and even more preferred is about 0.1 to about 10 mg/kg/day. Alternatively, the amount administered to an infant is from about 1 mg to about 10,000 mg/day, preferably abut 10 mg to about 1000 mg, and yet more preferred about 10 mg to about 500 mg.

The protein source that is present in addition to the dipeptide can be non-fat milk solids, a combination of non-fat milk solids and whey protein, a partial hydrolysate of non-fat milk and/or whey solids, soy protein isolates, or partially hydrolyzed soy protein isolates. The infant formula can be casein predominant or whey predominant.

Nutritionally complete compositions contain all vitamins and minerals understood to be essential in the daily diet and these should be present in nutritionally significant amounts. Those skilled in the art appreciate that minimum requirements have been established for certain vitamins and minerals that are known to be necessary for normal physiological function. Practitioners also understand that appropriate additional amounts (overages) of vitamin and mineral ingredients need to be provided to compensate for some loss during processing and storage of such compositions.

To select a specific vitamin or mineral compound to be used in the infant formula of the invention requires consideration of that compound's chemical nature regarding compatibility with the particular processing conditions used and shelf storage.

Examples of minerals, vitamins and other nutrients optionally present in the composition of the invention include vitamin A, vitamin $B_6$, vitamin $B_{12}$, vitamin E, vitamin K, vitamin C, folic acid, thiamine, inositol, riboflavin, niacin, biotin, pantothenic acid, choline, calcium, phosphorus, iodine, iron, magnesium, copper, zinc, manganese, chloride, potassium, sodium, selenium, chromium, molybdenum, taurine, and L-carnitine. Minerals are usually added in salt form. In addition to compatibility and stability considerations, the presence and amounts of specific minerals and other vitamins will vary somewhat depending on the intended infant population.

The infant formula of the invention also typically contains emulsifiers and stabilizers such as soy lecithin, carrageenan, and the like.

The infant formula of the invention may optionally contain other substances which may have a beneficial effect such as lactoferrin, nucleotides, nucleosides, immunoglobulins, and the like.

The infant formula of the invention is in concentrate liquid form, liquid ready to consume form, or powder form. Of course, if in powder form, the formula is diluted to normal strength with water to be in a form ready to consume.

The osmolality of the liquid infant formula of the invention (when ready to consume) can be about 100 to 300 mOsm/kg $H_2O$, more typically about 200 to 300 mOsm/kg $H_2O$.

The infant formula of the invention can be sterilized, if desired, by techniques known in the art, for example, heat treatment such as autoclaving or retorting, and the like.

The infant formula of the invention can be packaged in any type of container known in the art to be used for storing nutritional products such as glass, lined paperboard, plastic, coated metal cans and the like.

The infant formula of the invention is shelf stable after reconstitution. By "shelf stable" is meant that the formula in a form ready to consume remains in a single homogenous phase (i.e., does not separate into more than one phase upon visual inspection) or that the thickener does not settle out as a sediment upon visual inspection after storage overnight in the refrigerator. With the thickened nature of the product, the formula of the invention also has the advantage of remaining fluid (i.e., does not gel into a solid mass when stored overnight in the refrigerator).

The invention provides a commercially acceptable product in terms of desired stability and physical characteristics and the product demonstrates little to no observable browning effect by-products associated with a Maillard reaction. Further, the inventive composition is substantially homogeneous for an acceptable period after reconstitution (or for the shelf-life if prepared as a liquid). The invention is particularly useful for infant formula preparations for the prevention and treatment of retionoathy of prematurity, although it is equally applicable to other elemental diets specific to a selected population that is at risk of, or is suspected of having, diabetic retinopathy, vascular proliferative retinopathy, or proliferation of abnormal vascularization, and the like.

Example 11

Specific Compositions

For a serving size of 5 oz. the composition of the subject invention can comprise from a nutritional standpoint, for example, 2.5-10 grams of protein, less than 5 grams of fat, less than 10 grams of carbohydrates, and 130-135 grams (typically 134 grams) of water, as well as GLN, DHA, and butyrate. In one embodiment, the composition consists of the above-recited ingredients in the above-recited amounts and, optionally, vitamins, minerals, and nutrients. In another embodiment the composition can further comprise appropriate carries, preservatives, and the like that do not detract from the ability to safely administer the composition to an infant. Thus, the composition may comprise in addition to GLN, butyrate, and DHA, for example, any or all of the following (wherein the percentages are exemplary): nonfat milk, whey protein concentrate, mortierella alpina oil—a source of arachidonic acid—ARA—less than, crypthecodinium cohnii oil—a source of docosahexaenoic acid—DHA—less than, vitamin A palmitate—less than 1%, vitamin D3—less than 1%, vitamin E acetate—less than 1%, vitamin K1—less than 1%, thiamin hydrochloride—less than 1%, riboflavin—less than 1%, vitamin B6 hydrochloride—less than 1%, vitamin B12—less than 1%, niacinamide—less than 1%, folic acid—less than 1%, calcium pantothenate—less than 1% biotin—less than 1%, ascorbic acid—less than 1%, choline chloride—less than 1%, inositol—less than 1%, calcium carbonate—less than 1%, magnesium oxide—less than 1%, ferrous sulfate—less than 1%, zinc sulfate—less than 1%, manganese sulfate—less than 1%, cupric sulfate—less than 1%, potassium chloride—less than 1%, potassium citrate— less than 1%, potassium hydroxide—less than 1%, sodium selenite—less than 1%, taurine—less than 1%, L-carnitine—less than 1%, nucleotides—less than 1%, adenosine 5'-monophosphate—less than 1%, cytidine 5'-monophosphate—less than 1%, disodium guanosine 5'-monophosphate—less than 1%, disodium uridine 5'-monoposphate—less than 1%. Further, the amount per serving of various ingredients, in an exemplary embodiment, can be as follows (wherein it is understood that the amounts listed can be varied by 50% or more).

Linoleic Acid 860.0 mg
Vitamin A 300.0 IU
Vitamin D 60.0 IU
Vitamin E 2.0 IU
Vitamin K 8.0 mcg
Thiamin (Vitamin B1) 80.0 mcg
Riboflavin (Vitamin B2) 140.0 mcg
Vitamin B6 60.0 mcg
Vitamin B12 0.3 mcg
Niacin 1000.0 mcg
Folic Acid (Folacin) 16.0 mcg
Pantothenic Acid 500.0 mcg
Biotin 3.0 mcg
Vitamin C (Ascorbic Acid) 12.0 mg
Choline 24.0 mg
Inositol 6.0 mg
Calcium 78.0 mg
Phosphorus 43.0 mg
Magnesium 8.0 mg
Iron 1.8 mg
Zinc 1.0 mg
Manganese 15.0 mcg
Copper 75.0 mcg
Iodine 10.0 mcg
Selenium 2.8 mcg
Sodium 27.0 mg
Potassium 108.0 mg
Chloride 63.0 mg All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A nutritionally complete enteral neonate composition, comprising
   protein,
   a long chain polyunsaturated fatty acid,
   a short chain fatty acid comprising butyrate,
   glutamine,
   vitamin A, vitamin C, thiamin, riboflavin, niacin, calcium, iron, vitamin D, vitamin E, vitamin $B_6$, folic acid, vitamin $B_{12}$, phosphorus, iodine, magnesium, zinc, copper, biotin, and pantothenic acid.

2. The nutritionally complete composition, according to claim 1, wherein said long chain polyunsaturated fatty acid is docosahexaenoic acid (DHA).

3. The nutritionally complete composition, according to claim 1, wherein said short chain fatty acid consists of butyrate.

4. The nutritionally complete composition, according to claim 1, further comprising arginine.

5. The nutritionally complete composition, according to claim 1, comprising protein, DHA, butyrate and glutamine.

6. The nutritionally complete composition, according to claim 1, wherein the protein is whey.

7. The nutritionally complete composition, according to claim 1, which is hypo-osmolar.

8. The nutritionally complete composition, according to claim 1, wherein the composition is a minimal enteral nutrition formula.

9. A method for promoting gastrointestinal health in a neonate, wherein said method comprises administering to a neonate the composition according to claim 1.

10. The method, according to claim 9, wherein said long chain polyunsaturated fatty acid is DHA.

11. The method, according to claim 9, wherein said short chain fatty acid consists of butyrate.

12. The method, according to claim 9, wherein said nutritionally complete composition further comprises arginine.

13. The method, according to claim 9, wherein said nutritionally complete composition comprises protein, DHA, butyrate and glutamine.

14. The method, according to claim 9, wherein the protein is whey.

15. The method, according to claim 9, wherein the nutritionally complete composition is hypo-osmolar.

16. The method, according to claim 9, wherein the nutritionally complete composition is a minimal enteral nutrition formula.

17. The method, according to claim 9, wherein the neonate weights less than 1250 grams.

18. The composition according to claim 1, further comprising vitamin K, inositol, choline, manganese, chloride, potassium, sodium, selenium, chromium, molybdenum, taurine and L-carnitine.

19. The method according to claim 9, further comprising vitamin K, inositol, choline, manganese, chloride, potassium, sodium, selenium, chromium, molybdenum, taurine and L-carnitine.

* * * * *

UNITED STATES PATENT AND TRADEMARK OFFICE
CERTIFICATE OF CORRECTION

PATENT NO. : 9,107,894 B2
APPLICATION NO. : 12/682815
DATED : August 18, 2015
INVENTOR(S) : Josef Neu Page 1 of 1

It is certified that error appears in the above-identified patent and that said Letters Patent is hereby corrected as shown below:

IN THE SPECIFICATION

Column 4,
Line 61, "hyperpetineability" should read --hyperpermeability--.

Column 6,
Line 46, "transcpithelial" should read --transepithelial--.

Column 8,
Line 7, "villas height" should read --villus height--.

Signed and Sealed this
Fifteenth Day of March, 2016

Michelle K. Lee
*Director of the United States Patent and Trademark Office*